United States Patent [19]

Hamaguchi et al.

[11] Patent Number: 5,116,539
[45] Date of Patent: May 26, 1992

[54] REAGENT AND METHOD FOR MEASURING LEUKOCYTES AND HEMOGLOBIN IN BLOOD

[75] Inventors: Yukio Hamaguchi; Yukio Tsujino, both of Hyogo, Japan

[73] Assignee: TOA Medical Electronics Co., Ltd., Hyogo, Japan

[21] Appl. No.: 266,860

[22] Filed: Nov. 3, 1988

[30] Foreign Application Priority Data

Jan. 27, 1988 [JP] Japan .................. 63-16735

[51] Int. Cl.⁵ .............. G01N 31/00; C12Q 1/04
[52] U.S. Cl. ................. 252/408.1; 436/10; 435/34; 252/351
[58] Field of Search ........ 252/408.1, 351; 436/10; 435/34

[56] References Cited

U.S. PATENT DOCUMENTS

| | | | |
|---|---|---|---|
| 3,884,579 | 5/1975 | Mauthner | 356/39 |
| 4,099,917 | 7/1978 | Kim | 436/10 |
| 4,219,440 | 8/1980 | Runck et al. | 252/408 |
| 4,506,018 | 3/1985 | North | 436/10 |
| 4,529,705 | 7/1985 | Larsen | 436/17 |
| 4,610,961 | 9/1986 | Guardino et al. | 435/34 |
| 4,751,179 | 6/1988 | Ledis et al. | 435/34 |
| 4,801,549 | 1/1989 | Cremins et al. | 436/10 X |
| 4,902,613 | 2/1990 | Chang et al. | 435/2 |
| 4,968,629 | 11/1990 | Lapicola | 436/18 |

FOREIGN PATENT DOCUMENTS

| | | |
|---|---|---|
| 0003340 | 1/1979 | European Pat. Off. |
| 0115077 | 8/1984 | European Pat. Off. ........ 436/10 |
| 3729639 | 9/1987 | Fed. Rep. of Germany. |
| 8403771 | 9/1984 | World Int. Prop. O. |

Primary Examiner—Robert L. Stoll
Assistant Examiner—C. Harris
Attorney, Agent, or Firm—Nixon & Vanderhye

[57] ABSTRACT

A reagent for and method of measuring leukocytes or hemoglobin or both in blood using a reagent which is water-soluble mixture containing:

(a) a polyoxyethylene-based nonionic surfactant represented by the formula:

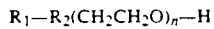

where $R_1$ is an alkyl, alkenyl or alkynyl group having 6 to 24 carbon atoms, $R_2$ is —O—,

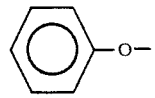

or —COO—, and n is an integer of 6 to 50, and (b) a buffer to adjust the pH of the solution within the range of 3-11 is disclosed. Measurements of hemoglobin in blood samples are of extreme importance to clinical diagnosis of such diseases as leukemia and anemia. Measurements of eosinophils, which are in the category of leukocytes, are important to the diagnosis of allergic conditions.

5 Claims, 4 Drawing Sheets

REAGENT AND METHOD FOR MEASURING LEUKOCYTES AND HEMOGLOBIN IN BLOOD

The present invention relates to a reagent for measuring leukocytes and hemoglobin in blood samples.

Measurements of leukocytes and hemoglobin in blood samples are of extreme importance to clinical diagnosis of such diseases as leukemia and anemia. Measurements of eosinophils which are in the category of leukocytes are important to the diagnosis of allergic diseases.

A standard technique of leukocyte measurements is the manual counting techniques which depend on observation under a microscope. However, this visual counting method is time-consuming and involves tedious procedures, particularly when one wants to count eosinophils, since it consists of diluting a blood sample with Hinkelman's solution, Randolph's solution or other diluting solutions that contain acidic dyes which lyse erythrocytes while selectively staining eosinophilic granules, and then counting individual eosinophils on a glass plate.

Automatic blood analyzers are also commonly employed for counting leukocytes in blood samples. Leukocyte counting with an automatic blood analyzer starts with lysing erythrocytes in a blood sample by addition of an erthrolytic agent so as to prepare a sample containing only the leukocytes left intact. This sample is allowed to pass through a small channel or fine orifice in the detecting portion of the analyzer. The number of leukocytes is counted by detecting electrical or optical signals that are generated in response to the passage of individual leukocytes.

A more sophisticated apparatus has recently been developed that counts different types of leukocytes including granulocytes, monocytes and lymphocytes as classified by the difference in intensity of the signals obtained. An apparatus is also commercially available that counts granulocytes as classified into neutrophils, eosinophils and basophils. This apparatus enables eosinophils to be counted much more easily than the visual counting method.

Hemoglobin measurements are commonly performed by first converting blood hemoglobin to cyanmethemoglobin (HiCN) by the action of a lytic agent containing potassium ferricyanide and cyan and then measuring its absorbance at a specific wavelength. This method, which is generally referred to as the cyanmethemoglobin method, or a modification thereof, may also be employed for automatic blood analysis since the sample for leukocyte measurements that is described above is directly usable as a sample for hemoglobin measurement.

A problem with the cyanmethemoglobin method is that handling the reagent involves safety hazards since the reagent contains toxic cyan. In addition, the waste liquor resulting from measurements has to be disposed of after the cyan in it is decomposed with a suitable chemical such as sodium hypochlorite. With a view to eliminating these disadvantages, a method has been proposed in which blood hemoglobin is converted to oxyhemoglobin (HbO$_2$) and its absorbance is measured at a specific wavelength. This method, generally referred to as the oxyhemoglobin method, does not use cyan and hence involves no safety hazards in terms of handling the reagent. Furthermore, the resulting waste liquor can be disposed of in a very simple way.

However, the conventional oxyhemoglobin method has a disadvantage in that the lytic reagent not only lyses erythrocytes but also reduces the size of leukocytes to a very small one. This is favorable for the purpose of absorbance measurements since it minimizes the scattering of light by leukocytes but, on the other hand, it becomes impossible to measure leukocytes with the lytic reagent.

To avoid this problem, blood analyses with automatic analyzers by the oxyhemoglobin method have been performed by passing separately prepared samples for hemoglobin and leukocytes through two detecting portions, one for hemoglobin measurement and the other for leukocyte measurement. However, this approach suffers the disadvantages of requiring complex equipment and in curing high costs, because not only are two separate detecting portions necessary but also two fluid lines are required in preparing samples for measurement.

If with an automatic blood analyzer that is furnished with a detecting portion for eosinophil measurements, hemoglobin can be measured in that detecting portion by the oxyhemoglobin method, the need to provide a separate detecting portion for hemoglobin measurement is eliminated, leading to simplification of the overall composition of the equipment. Leukocyte counting may be performed as in the detecting portion for leukocyte measurement as in the prior art.

However, even an automatic blood analyzer that is furnished with a detecting portion for classifying leukocytes into eosinophils and other types is unable to measure hemoglobin using a sample for leukocyte classification (or a sample for eosinophil measurement). A need has therefore arisen for the development of a reagent that allows simultaneous measurements of leukocytes or even eosinophils in a sample prepared for performing the oxyhemoglobin method. A further benefit would be offered by such a reagent if its use enabled counting of leukocytes as classified into other types including granulocytes, monocytes and lymphocytes.

The present invention meets the above-stated needs by providing a reagent for measuring leukocytes and hemoglobin in blood which is a water-soluble mixture containing the following components (a) and (b):

(a) a polyoxyethylene based nonionic surfactant represented by the following general formula: $R_1$—$R_2$—$(CH_2CH_2O)_n$—H (where $R_1$ is an alkyl, alkenyl or alknyl group having 6-24 carbon atoms; $R_2$ is —O—,

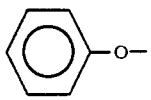

or —COO; and n is an integer of 6-50); and (b) a buffer agent that adjusts the pH of an aqueous solution to be within the range of 3-11.

If this reagent is to be used for the specific purpose of eosinophil measurements, the buffer agent is one that is capable of adjusting the pH of an aqueous solution to be within the range of 5-11.

If the reagent is to be used in distinguishing between lymphocytes and other types of leukocytes or distinguishing between lymphotyctes, granulocytes and other types of leukocytes, n in the general formula of the polyoxyethylene based nonionic surfactant is an integer of 10-30, and $R_1$ is an alkyl, alkenyl or alkynyl group having 10-20 carbon atoms.

When the reagent of the present invention is added to blood, the erythrocytes in the blood are lysed momentarily and hemoglobin is immediately converted to oxyhemoglobin, thereby enabling hemoglobin to be measured. The erythrocyte ghosts which remain after the erythrolysis as well as platelets are reduced in size to such an extent that they can be clearly distinguished from leukocytes with an automatic blood analyzer.

Leukocytes in the blood gradually decrease in size after the addition of the reagent but they retain for a certain period of time sufficient size to be clearly detected with the automatic analyzer. Therefore, the number of leukocytes can be counted by performing a measurement within that certain period of time. After the lapse of this period, the nuclei of all leukocytes other than eosinophils become naked, while those of eosinophils remain intact, thereby enabling the eosinophils to be selectively detected by the automatic analyzer.

If the reagent of the present invention is such that n in its general formula is an integer of 10-30 and $R_1$ is an alkyl, alkenyl or alkynyl group having 10-20 carbon atoms, analysis with an automatic blood analyzer allows a sufficient time during which leukocytes can be consistently classified as lymphocytes and other types, or lymphocytes, monocytes and other types depending upon the difference in intensity of detected signals. Classification and counting of leukocytes can be accomplished if measurements are completed within this period of time.

If a sample that is prepared using the reagent of the present invention has a pH in the range of 3-11, not only can the measurement of leukocytes in blood be accomplished, but also the counting of classified leukocytes, and in addition, hemoglobin measurements are also possible. The sample preferably has a pH of 4-9 in order to allow leukocytes to be classified and counted in a more efficient way. For eosinophil measurements, the pH range of 5-11 is preferred.

The following examples are given to show exemplary compositions of the reagent of the present invention, as well as measurements that employ such compositions.

EXAMPLE 1

Composition of Reagent

| | |
|---|---|
| Polyoxyethylene based nonionic surfactant $C_{18}H_{35}$—O—$(CH_2CH_2O)_{12}$—H | 0.4 g |
| Buffer agent | |
| $Na_2HPO_4 \cdot 12H_2O$ | 0.28 g |
| $KH_2PO_4$ | 0.02 g |
| Osmotic pressure adjusting agent (NaCl) | 0.37 g |
| Preservative (sodium salt of 2-pyridylthio-1-oxide) | 0.02 g |
| Water | 100 ml |

Figure 1:
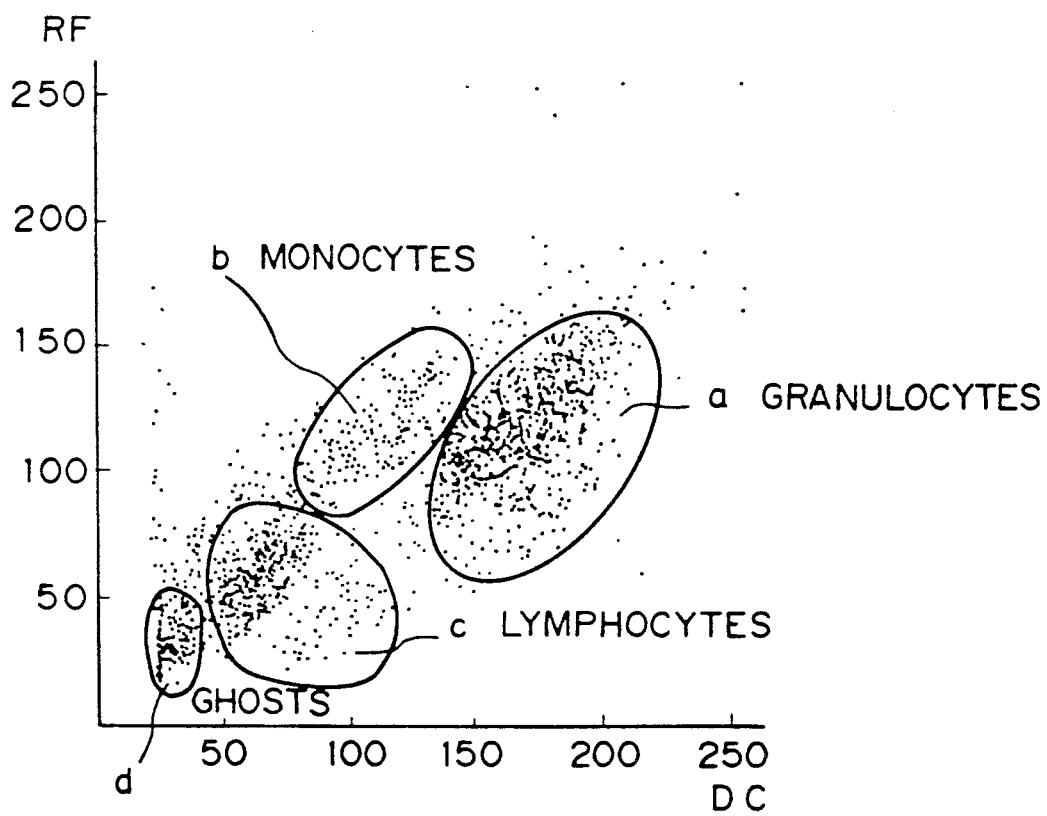
FIG. 1 is a two-dimentional distribution diagram showing the results of classification of leukocytes in Example 1.

A blood sample diluted with a reagent having the above-specified composition was subjected to a leukocyte measurement for 6 seconds at a pH of 7.5 and an osmotic pressure of 160 mOsm with the temperature of the sample solution held at 26° C. The measurement started 13 seconds after the addition of the reagent. The results are shown in FIG. 1. The x-axis of the two-dimensional distribution diagram shown in FIG. 1 plots the intensity of relative signals as obtained when the measurement was conducted by the DC method, and the y-axis plots the intensity of relative signals as obtained when the measurement was conducted by the RF method.

The DC method detects any change that occurs in electric current on account of the difference in conductivity between particles and the fluid medium in which they are suspended when a sample formed of the suspension is allowed to pass through a narrow fluid channel. In this DC method, the intensity of a signal detected is substantially proportional to the volume of particles. In the RF method, a sample prepared by suspending particles in a fluid medium having a different dielectric constant is allowed to pass through a fluid channel having a constructed portion held between closely adjacent electrodes and the change that occurs in the electric impedance between the electrodes on account of the difference in dielectric constant between the particles and the fluid medium is detected. In this RF method, the intensity of a signal detected reflects not only information related to the size of particles but also information related to their structure and the nature of the material of which they are made.

The dots in FIG. 1 represent the cells that produced DC and RF signals the intensities of which were respectively associated with the DC and RF methods. As shown in FIG. 1, leukocytes are divided into three populations, a, b and c, which correspond to granulocytes, monocytes and lymphocytes, respectively. The identity of each population was established by analyzing samples which contained individually separated leukocyte species and by testing the correlation with the visual counting method. A population of erythrocyte ghosts is denoted by d in FIG. 1. The sum of the number of cells included within the populations of granulocytes, monocytes and lymphocytes was in agreement with the number of leukocytes counted by the conventional visual method.

The above results show that the reagent of the present invention enables not only the counting of leukocytes in blood but also counting of them once classified into granulocytes, monocytes and lymphocytes. In Example 1, two electrical methods of detection called the DC and RF methods were employed. It should, however, be noted that an optical method of detection can also be used. If the number of lymphocytes is the only information to be obtained, one only needs to classify leukocytes into lymphocytes and other types.

Figure 2:
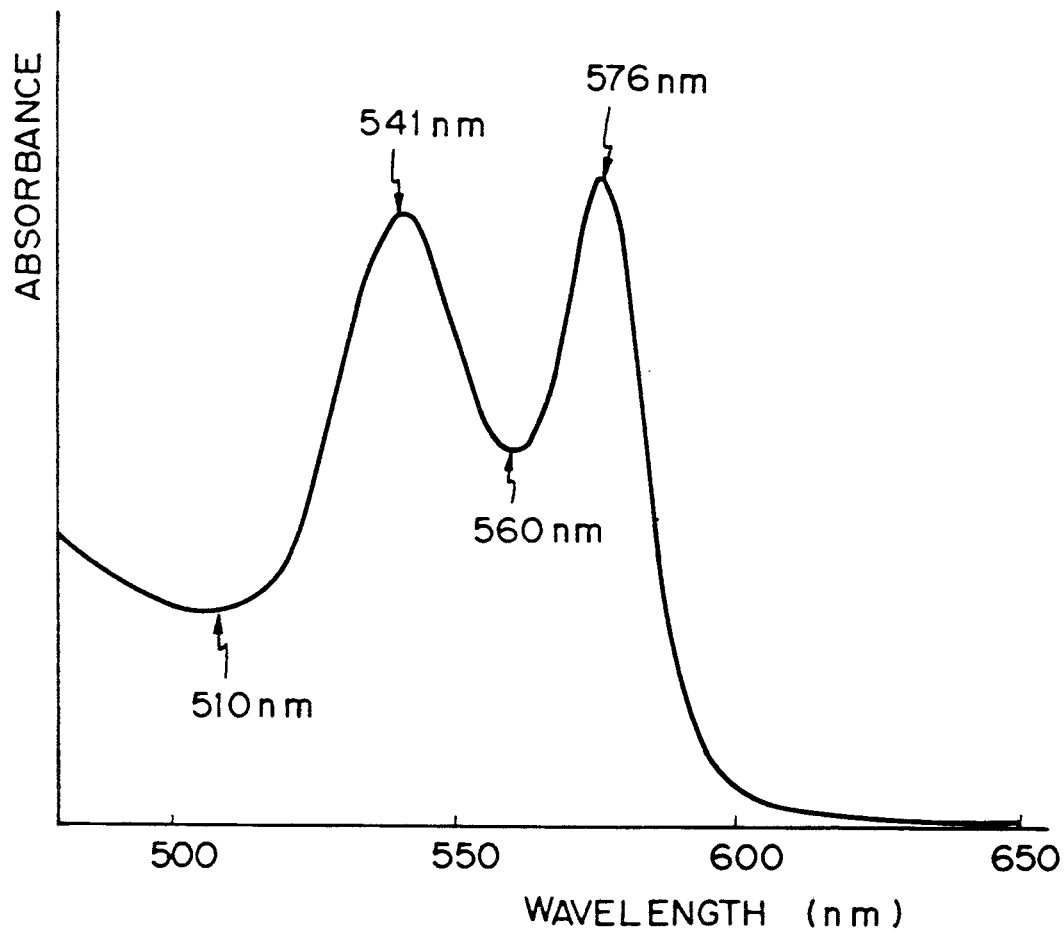
FIG. 2 shows a hemoglobin absorption curve as obtained in Examples 1 and 2.

An absorption curve was obtained for a sample which was the same as what was subjected to the leukocyte measurement above using a reagent of the composition also shown above. The curve is shown in FIG. 2, in which the x-axis plots the wavelength and the y-axis plots the absorbance. The wavelength maxima (541 nm and 576 nm) and minima (510 nm and 560 nm) on the absorption curve were in agreement with the absorption wavelengths for oxyhemoglobin that are documented in references such as "Ketsueki Kensa (Blood Testing)" edited by S. Miwa, vol. 3 of "Rinsho Kensa Gijutsu Zensho (Encyclopedia of Clinical Testing Techniques)", pp 46-52, 1976. It was thus established that the addition of the reagent of the present invention had caused conversion of blood hemoglobin to oxyhemoglobin.

In Example 1, the leukocyte measurement was started 13 seconds after the addition of the reagent. It should, however, be noted that a hemoglobin measurement can be performed right after the addition of this reagent. Therefore, the present invention enables the necessary measurement to be completed within a very short period of time as compared with the cyanmethemoglobin method which requires 3-5 minutes for the conversion of hemoglobin to cyanmethemoglobin. In a case where there is no need to classify leukocytes and one only needs to obtain leukocyte counts, it is possible to start the measurement several seconds after the addition of the reagent, provided that such conditions as the temperature of the sample solution are appropriately selected.

EXAMPLE 2

Composition of Reagent

| Polyoxyethylene based nonionic surfactant | |
| --- | --- |
| $C_{16}H_{33}$—O—$(CH_2CH_2O)_{14}$—H | 1.3 g |
| $C_{18}H_{35}$—O—$(CH_2CH_2O)_{13}$—H | 1.17 g |
| Buffer agent $Na_2HPO_4 \cdot 12H_2O$ | 4.0 g |
| Osmotic pressure adjusting agent (NaCl) | 0.4 g |
| Preservative (sodium salt of 2-pyridylthio-1-oxide) | 0.02 g |
| Water | 100 ml |

Figure 3:
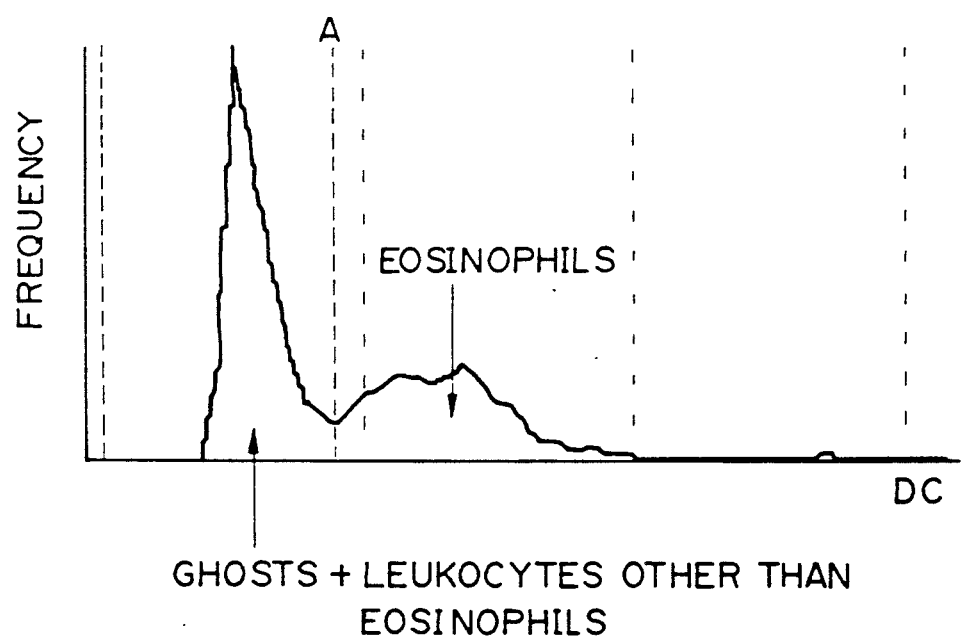
FIG. 3 is a distribution diagram showing the results of eosinophil measurement conducted in Example 2.

A blood sample diluted with a reagent having the above-specified composition was subjected to an eosinophil measurement for 6 seconds at a pH of 7.5 and an osmotic pressure of 160 mOsm with the temperature of the sample solution held at 40° C. The measurement started 50 seconds after the addition of the reagent. The results are shown in FIG. 3. The x-axis of the graph shown in FIG. 3 plots the intensity of relative signals as obtained when the measurement was conducted by the DC method, and the y-axis plots the frequency for cells having a certain intensity of DC signals.

The dashed line A in FIG. 3 represents the threshold level at which eosinophils are separated from other cells. The population on the right side of line A is that of eosinophils and their number can be determined by counting the number of cells included in this population. The population on the left side of line A includes erythrocyte ghosts and the naked nuclei of leukocytes other than eosinophils.

Figure 4:
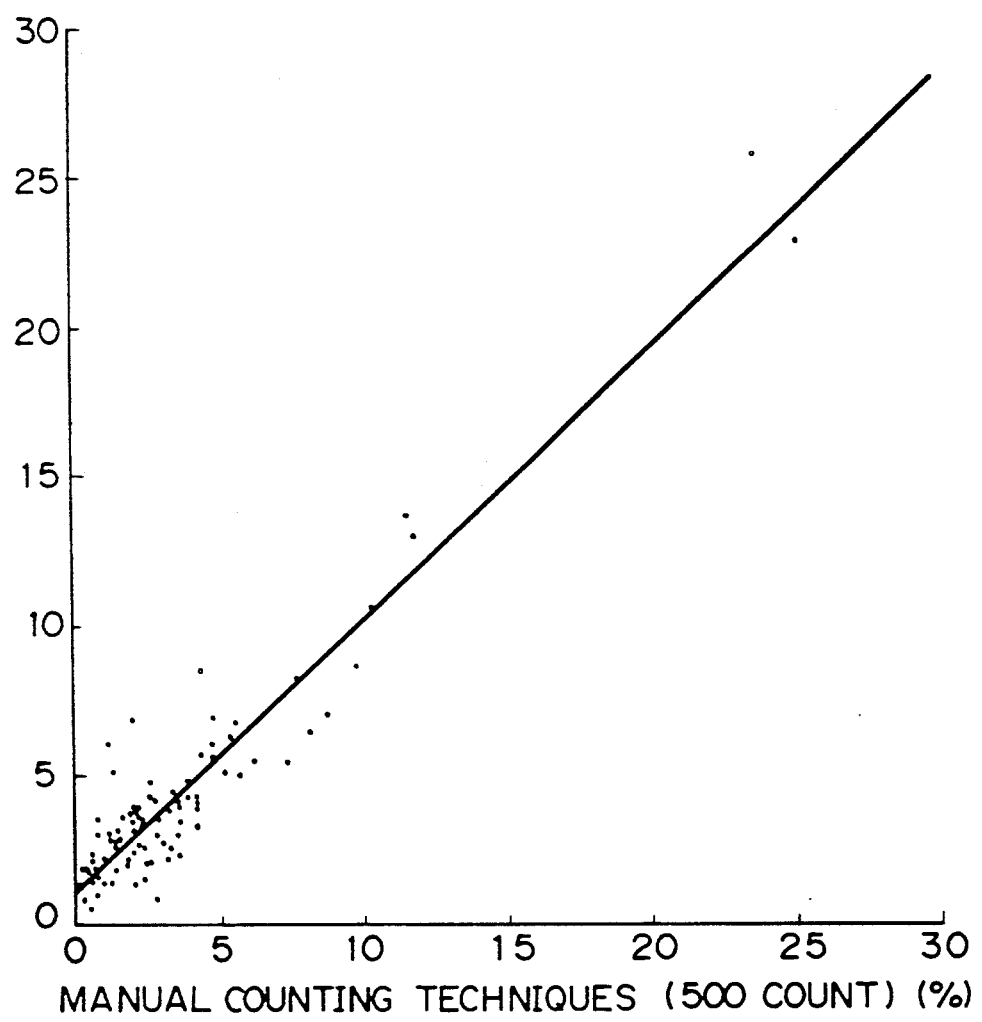
FIG. 4 is a graph showing the correlation between the results of eosinophil measurement conducted in Example 2 and those of measurement performed by the conventional manual counting techniques.

FIG. 4 shows the correlation of the so determined number of eosinophils and that of eosinophils as determined by the conventional manual counting techniques. The x-axis of the graph shown in FIG. 4 plots the percentage of 500 cells in one sample that were identified as eosinophils by the visual method. The y-axis plots the percentage of leukocytes that were counted as eosinophils with an automatic blood analyzer using the reagent of the present invention, with the leukocyte count being obtained with the same analyzer by a known method. The number of samples analyzed was 105. The coefficient of correlation was 0.9453 and the reagression line was Y=0.9149×1.0651, which is drawn as the straight line in FIG. 4. The good correlation between the method using the reagent of the present invention and the conventional method establishes the reliability of measuring eosinophils using the reagent of the present invention.

In Example 2, an electrical method of detection called the DC method was employed. It should, however, be noted that other electrical methods of detection can also be used as well as an optical method.

An absorption curve was obtained for a sample which was the same as what was subjected to the eosinophil measurement above using a reagent of the composition also shown above. The curve was the same as shown in FIG. 2.

In Example 2, the eosinophil measurement was started 50 seconds after the addition of the reagent. It should, however, be noted that a hemoglobin measurement can be performed right after the addition of the reagent. The present invention thus enables the necessary measurement to be completed within a very short period of time as compared with the cyanmethomoglobin method which requires 3-5 minutes for the conversion of hemoglobin to cyanmethemoglobin. The higher the pH of the sample to be analyzed, the more rapidly can the nuclei of leukocytes other than eosinophils be made naked, thereby further shortening the time before eosinophil measurement can be started. It should be mentioned that the time at which an eosinophil measurement can be started also varies with the temperature of a sample solution.

The reagent of the present invention offers the following advantages. Firstly, it enables leukocytes and hemoglobin in blood to be measured simultaneously using the same sample. Since hemoglobin is measured by the oxyhemoglobin method, the reagent can be handled without any safety hazard and the waste liquor resulting from the measurement can be disposed of in a simple way. Secondly, the reagent of the present invention enables classified counting of leukocytes in blood to be performed simultaneously with a hemoglobin measurement by the oxyhemoglobin method using the same sample. Thirdly, a hemoglobin measurement can be performed right after the addition of the reagent whereas a leukocyte measurement cannot be started until after a period ranging from several seconds to ten-odd seconds following the addition of the reagent. Therefore, this reagent contributes to faster measurements with an automatic blood analyzer.

What is claimed is:

1. A method of measuring both leukocytes and hemoglobin at the same time comprising:

(1) contacting a blood sample with a water-soluble reagent consisting essentially of an aqueous solution of:

(a) a polyoxyethylene-based nonionic surfactant represented by the formula:

$$R_1—R_2—CH_2CH_2O)_n—H$$

where $R_1$ is an alkyl, alkenyl or alkynyl group having 6 to 24 carbon atoms, $R_2$ is —O—,

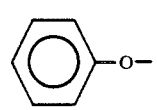

or —COO—, and n is an integer of 6 to 50, and (b) a buffer to adjust the pH of the solution within the range of 3-11, and thereafter (2) counting the thus-treated blood sample in an automated blood analyzer.

2. The method of claim 1, in which the hemoglobin is measured and the reagent treated blood sample is analyzed immediately after contacting the reagent and converting the hemoglobin to oxyhemoglobin.

3. The method of claim 1, in which blood leukocytes are counted and classified.

4. The method of claim 3, in which n has a value of 10 to 30 and $R_1$ is an alkyl, alkenyl or alkynyl group having 10 to 20 carbon atoms.

5. A method of measuring eosinphils in a blood sample comprising:
(1) contacting a blood sample with a water-soluble reagent consisting essentially of an aqueous solution of:
(a) a polyoxyethylene-based nonionic surfactant represented by the formula:

$$R_1-R_2-CH_2CH_2O)_n-H$$

where $R_1$ is an alkyl, alkenyl or alkynyl group having 6 to 24 carbon atoms, $R_2$ is —O—,

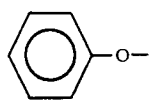

or —COO—, and n is an integer of 6 to 50, and
(b) a buffer to adjust the pH of the solution within the range of 3-11,
(2) allowing the reagent to lyse all leukocytes other than the eosinophils, and thereafter
(3) counting the intact eosinophils.

* * * * *